United States Patent
Costa et al.

(10) Patent No.: US 7,563,570 B2
(45) Date of Patent: Jul. 21, 2009

(54) METHOD OF DETERMINING A CHEMOTHERAPEUTIC REGIMEN FOR NON SMALL CELL LUNG CANCER BASED ON BRCA1 EXPRESSION

(75) Inventors: Rafael Rosell Costa, Barcelona (ES); Miquel Taron Roca, Sant Cugat del Vallés (ES)

(73) Assignee: Pangaea Biotech, Barcelona (ES)

( * ) Notice: Subject to any disclaimer, the term of this patent is extended or adjusted under 35 U.S.C. 154(b) by 249 days.

(21) Appl. No.: 10/977,951

(22) Filed: Oct. 29, 2004

(65) Prior Publication Data

US 2006/0094021 A1 May 4, 2006

(51) Int. Cl.
*C12Q 1/68* (2006.01)
(52) U.S. Cl. .......................... 435/6; 435/91.1; 536/23.2; 536/24.33
(58) Field of Classification Search ...................... 435/6, 435/91.1; 536/23.1, 24.33
See application file for complete search history.

(56) References Cited

U.S. PATENT DOCUMENTS

| | | | |
|---|---|---|---|
| 4,808,614 A | 2/1989 | Hertel | |
| 5,464,826 A | 11/1995 | Grindey et al. | |
| 5,562,925 A | 10/1996 | Rosenberg et al. | |

FOREIGN PATENT DOCUMENTS

WO    WO 02/088354 A1    11/2002

OTHER PUBLICATIONS

An.Q.et.al. Deletion of tumor suppressor genes in chinese non-small cell lung cancer. Cancer lett. 2002. 184: 189-195.*
Zeng-Rong.et.al. Elevated DNA repair capacity is accociated with intrinsic resistance to lung cancer to chemotherapy. Cancer.Res. 1995. 55: 4760-64.*
Quinn.J.E.et.al. BRCA1 functions as a differential modulator of chemotherapy-induced apoptosis. Cancer Res. 2003. 63: 6221-28.*
Tassone.P.et.al BRCA1 expression modulates chemosensitivity of BRCA1-defective HCC1937 human breast cancer cells. Br.J.cancer. 2003. 88: 1285-91.*
Bhattacharya.A.et.al. The breast cancer susceptibility gene BRCA1 is required for subnuclear assembly of Rad51 and survival following treatment with DNA cross-linking agent cisplatin. JBC. 2000. 275: 23899-23903.*
Mayer.A.et.al. The prognostic significance of proliferating cell nuclear antigen, epidermal growth factor receptor and mdr gene expression in colorectal cancer. Cancer.1993. 71: 2454-60.*
Stedman's medical dictionary, 25th ed, 1990, p. 1652-1653.*
Taron et al, Aug. 2004, Human Mol Genetics, 13(2): 2443-2449.*
MacLachlan et al, 2000, JBC, 275(4): 2777-85.*
Taron M, Rosell R, Felip E, Mendez P, Souglakos J, Ronco MS, Queralt C, Majo J, Sanchez JM, Sanchez JJ, Maestre J, "BRCA1 mRNA expression levels as an indicator of chemoresistance in lung cancer," *Hum Mol Genet*, vol. 13(20), pp. 2443-2449, Oct. 15, 2004, Epub Aug. 18, 2004.
Pass HI, et al., "Randomized trial of neoadjuvant therapy for lung cancer: interim analysis," *Ann. Thor. Surg.*, vol. 53, pp. 992-998, 1992.
Rosell R, et al., "A randomized trial comparing preoperative chemotherapy plus surgery with surgery alóne in patients with non-small-cell lung cancer," *N. Engl. J. Med.*, vol. 330, pp. 153-158, 1994.
Kennedy RD, et al., "BRCA1: mechanisms of inactivation and implications for management of patients," *Lancet*, vol. 360, pp. 1007-1014, 2002.
Husain A, et al., "BRCA1 up-regulation in associated with repair-mediated resistance to cis-diamminedichloroplatinum(II)," *Cancer Res.*, vol. 58, pp. 1120-1123, 1998.
Lafarge S, et al., "Inhibition of BRCA1 leads to increased chemoresistance to microtubule-interfering agents, an effect that involves the JNK pathway," *Oncogene*, vol. 20, pp. 6597-6606, 2001.
Seery LT, et al., "BRCA1 expression levels predict distant metastasis of sporadic breast cancers," *Int. J. Cancer (Pred. Oncol.)*, vol. 84, pp. 258-262, 1999.
Egawa C., "Decreased expression of BRCA2 mRNA predicts favorable response to docetaxel in breast cancer," *Int. J. Cancer (Pred. Oncol.)*, vol. 95, pp. 255-259, 2001.
Specht K, et al., "Quantitative gene expression analysis in microdissected archival formalin-fixed and paraffin-embedded tumor tissue," *Am. J. Pathol.*, vol. 158, pp. 419-429, 2001.
Krafft AE, et al., "Optimization of the isolation and amplification of RNA from formalin fixed, paraffin-embedded tissue: The Armed Forces Institute of Pathology experience and literature review," *Mol. Diagn.*, vol. 3, pp. 217-230, 1997.

* cited by examiner

*Primary Examiner*—Larry R. Helms
*Assistant Examiner*—Minh-Tam Davis
(74) *Attorney, Agent, or Firm*—Locke Lord Bissell & Liddell, LLP

(57) ABSTRACT

The present invention relates to a screening method for classifying patients and for selecting an effective chemotherapy for the treatment of a patient suffering from non-small-cell lung cancer (NSCLC), based on the use of his levels of BRCA1 expression to predict the outcome of chemotherapy.

5 Claims, 5 Drawing Sheets

METHOD OF DETERMINING A CHEMOTHERAPEUTIC REGIMEN FOR NON SMALL CELL LUNG CANCER BASED ON BRCA1 EXPRESSION

FIELD OF THE INVENTION

The present invention relates to the use of BRCA1 levels of expression as a prognostic marker of chemotherapy response in non small cell lung carcinoma (NSCLC) patients, to methods of selecting chemotherapy and of classifying patients accordingly, and to the use of chemotherapeutic agents for the treatment of NSCLC patients.

BACKGROUND OF THE INVENTION

Non-small-cell lung cancer (NSCLC) accounts for approximately 80% of all lung cancers, with 1.2 million new cases worldwide each year. NSCLC resulted in more than one million deaths worldwide in 2001 and is the leading cause of cancer-related mortality in both men and women (31% and 25%, respectively). The prognosis of advanced NSCLC is dismal. A recent Eastern Cooperative Oncology Group trial of 1155 patients showed no differences among the chemotherapies used: cisplatin/paclitaxel, cisplatin/gemcitabine, cisplatin/docetaxel and carboplatin/paclitaxel. Overall median time to progression was 3.6 months, and median survival was 7.9 months.

The overall five-year survival of patients with NSCLC has remained at less than 15% for the past 20 years. Stage grouping of TNM subsets (T=primary tumor; N=regional lymph nodes; M=distant metastases) permits the identification of patient groups with similar prognosis and treatment options. Five-year survival is around 25% for pathologic stage IIB (T1-2N1M0, T3N0M0), 13% for stage IIIA (T3N1M0, T1-2-3N2M0), and a low 7% for stage IIIB (T4N0-1-2M0).

Currently, cisplatin (DDP) and carboplatin are among the most widely used cytotoxic anticancer drugs. However, resistance to these drugs through de novo or induced mechanisms undermines their curative potential. These drugs disrupt DNA structure through formation of intrastrand adducts. Resistance to platinum agents such as DDP has been attributed to enhanced tolerance to platinum adducts, decreased drug accumulation, or enhanced DNA repair.

Small randomized studies of cisplatin-based chemotherapy followed by surgery in clinical stage IIIA (Pass HI, et al. (1992) *Ann. Thor. Surg.*, 53, 992-998: "*Randomized trial of neoadjuvant therapy for lung cancer: interim analysis*") or stage IIB-IIIB (Rosell R, et al. (1994) *N. Engl. J. Med.*, 330, 153-158 "*A randomized trial comparing preoperative chemotherapy plus surgery with surgery alone in patients with non-small-cell lung cancer*") showed remarkable improvement in survival over NSCLC patients treated either with surgery alone or with surgery followed by radiotherapy. Event-free survival was similar in the two studies (12.7 and 20 months in the neoadjuvant chemotherapy arm and 5.8 and 5 months in the surgery arm). In general, neoadjuvant chemotherapy induces tumor shrinkage and sterilizes metastatic lymph nodes, leading to pathologic downstaging in approximately 33% and complete pathologic remission in up to 14% of patients.

During the past 30 years medical oncologists have focused to optimise the outcome of cancer patients and it is just now that the new technologies available are allowing to investigate polymorphisms, gene expression levels and gene mutations aimed to predict the impact of a given therapy in different groups of cancer patients to tailor chemotherapy. Representative examples include the relation between the TS mRNA expression and the response and the survival with antifolates (see EP 1 381 691), beta tubulin III mRNA levels and response to tubulin interacting agents, PTEN methylation and resistance to CPT-11 and STAT3 over expression and resistance to EGF interacting agents.

Although a wealth of data indicates that changes in the level of several gene transcripts can modulate differential chemosensitivity between NSCLC patients with the same TNM subset, at present no predictive genetic markers of chemotherapy response are used for tailoring treatment. To further improve the survival rate in patients with Non-Small Cell Lung Carcinoma (NSCLC), their prognostic classification based on molecular alterations is crucial. Such classification will provide more accurate and useful diagnostic tools and, eventually, more effective therapeutic options.

Breast Cancer 1 (BRCA1) plays a crucial role in DNA repair, and decreased BRCA1 mRNA expression has been observed in both sporadic and hereditary breast cancers (Kennedy R D, et al. (2002) *Lancet*, 360, 1007-1014: "*BRCA1: mechanisms of inactivation and implications for management of patients*"). However, its potential effect in lung cancer has never been examined.

BRCA1 is implicated in transcription-coupled nucleotide excision repair (TC-NER), and modulation of its expression leads to modification of TC-NER and hence to radio- and chemoresistance. Upregulation of BRCA1 expression led to increased cisplatin resistance in the SKOV-3 human ovarian cancer cell line (Husain A, et al. (1998) *Cancer Res.*, 58, 1120-1123: "*BRCA1 up-regulation is associated with repair-mediated resistance to cis-diamminedichloroplatinum(II)*"), and restoration of BRCA1 in the BRCA1-negative HCC1937 human breast cancer cell line restored radioresistance. BRCA1 is also involved in homologous recombination repair (HRR) and non-homologous end joining in response to DNA damage. In addition, it is a component of a large DNA repair complex termed the BRCA1-associated genome surveillance complex, which contains a number of mismatch repair proteins, indicating a potential role for BRCA1 in mismatch repair. BRCA1 may also be a regulator of mitotic spindle assembly, as BRCA1 and β-tubulin colocalize to the microtubules of the mitotic spindle and to the centrosomes. Finally, enhanced BRCA1 expression has been linked to apoptosis through the c-Jun N-terminal kinase pathway, which is activated by cisplatin-induced DNA damage; inhibition of this pathway increased cisplatin sensitivity in cell lines. Decreased BRCA1 mRNA expression in a breast cancer cell line, as determined by real-time quantitative polymerase chain reaction (RT-QPCR), led to greater sensitivity to cisplatin and etoposide but to greater resistance to the microtubule-interfering agents paclitaxel and vincristine (Lafarge S, et al. (2001) *Oncogene*, 20, 6597-6606: "*Inhibition of BRCA1 leads to increased chemoresistance to microtubule-interfering agents, an effect that involves the JNK pathway*"). Recently, reconstitution of wild-type BRCA1 into the BRCA1-negative HCC1937 breast cancer cell line resulted in a 20-fold increase in cisplatin resistance and, in contrast, in a 1000-10,000-fold increase in sensitivity to antimicrotubule drugs (paclitaxel and vinorelbine).

Mouse models carrying conditional disruption of BRCA1 were highly sensitive to doxorubicin and gamma irradiation but resistant to tamoxifen, providing additional evidence for differential chemosensitivity linked to BRCA1 expression. When BRCA1 expression was examined by semi-quantitative PCR in women with sporadic breast cancer, lower BRCA1 mRNA levels (bottom quartile) were associated with a higher frequency of distant metastases (Seery L T, et al.

(1999) Int. J. Cancer (Pred. Oncol.), 84, 258-262: "BRCA1 expression levels predict distant metastasis of sporadic breast cancers".

Despite the wealth of data in cell lines and mouse models, only one small study has examined the correlation of BRCA1 and BRCA2 mRNA expression with response to chemotherapy in the clinical setting (Egawa C., (2001) Int. J. Cancer (Pred. Oncol.), 95, 255-259: "Decreased expression of BRCA2 mRNA predicts favorable response to docetaxel in breast cancer"). Among 25 women with docetaxel-treated locally advanced or metastatic breast cancer, only BRCA2 mRNA levels were significantly lower in responders than in non-responders, though a slight difference was also observed for BRCA1.

SUMMARY OF THE INVENTION

It is an object of the invention to provide a tool for use in predicting differential chemosensitivity and tailoring chemotherapy in NSCLC. We have found that BRCA1 mRNA expression level is a good marker of differential sensitivity, providing an important tool for customizing NSCLC chemotherapy in order to improve survival in this very common and fatal disease.

In one aspect the present invention provides a screening method for selecting an effective chemotherapy for the treatment of a patient suffering from non-small-cell lung cancer (NSCLC), comprising the steps:

a) isolating mRNA from a tissue sample of the patient;

b) determining a gene expression level of BRCA1 in the sample;

c) comparing the BRCA1 gene expression levels in the sample with a predetermined threshold level for the BRCA1 gene expression;

d) and selecting a chemotherapeutic treatment selected from the group formed by cisplatin, carboplatin, gemcitabine, paclitaxel, docetaxel and combinations thereof, based on results of the comparison of the BRCA1 gene expression level with the predetermined threshold level.

In a second aspect the invention provides a method for classifying patients suffering from non-small-cell lung cancer comprising:

a) isolating mRNA from a tissue sample of the patient;

b) determining a gene expression level of BRCA1 in the sample;

c) comparing the BRCA1 gene expression levels in the sample with predetermined threshold levels for the BRCA1 gene expression;

d) and classifying the patients in 3 groups defined as "low", "normal" or high" according to the results of the comparison of the BRCA1 gene expression level with the predetermined threshold level.

In one embodiment the patient is suffering NSCLC prior to surgery.

In another embodiment the predetermined threshold level is obtained by dividing in 4 quartiles the levels of expression of BRCA1 measured in a collection of tumor tissue in biopsy samples from NSCLC patients, previous to the neoadjuvant chemotherapeutic treatment and defining a level of "low" for the bottom quartile, "normal" for the the middle quartiles or "high" for the top quartile of BRCA1 levels of expression.

To give good results the collection has at least 40 samples, more preferably at least 50 samples. It is preferred that the tissue sample is a fixed and paraffin-embedded sample.

The invention is also directed to the use of cisplatin as a single agent or as a gemcitabine/cisplatin combination in the manufacture of a medicament for the treatment of a NSCLC patient having low expression levels of the BRCA1 gene.

In another aspect the invention provides the use of docetaxel or paclitaxel as single agent or a combination of gemcitabine/paclitaxel or gemcitabine/docetaxel in the manufacture of a medicament for the treatment of a NSCLC patient having high expression levels of the BRCA1 gene.

DETAILED DESCRIPTION OF THE INVENTION

Figure 1A:
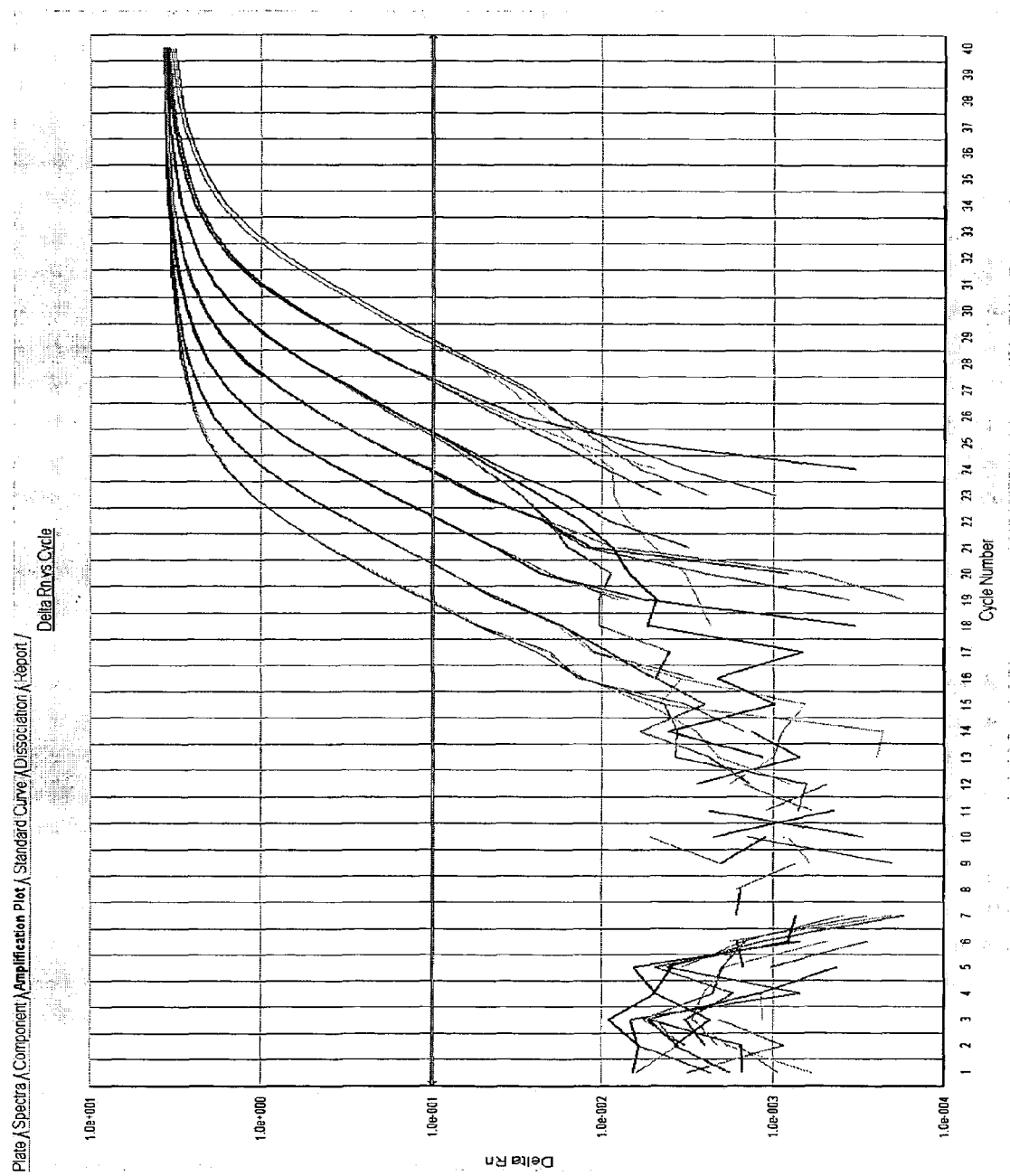
FIG. 1. Example of the amplification plots ($\Delta$Rn versus cycle number) of $\beta$-actin (A) and BRCA1 (B) cDNA. Both figures correspond to serial dilutions of cDNA obtained from one of the samples. C and D show examples of the validation curves for relative quantification. Different primers and probe concentrations were assayed for $\beta$-actin and BRCA1 gene expression analysis to obtain the optimal PCR efficiency. In order for the relative quantification to be valid, the amplification efficiency of the target (BRCA1) and the reference ($\beta$-actin) amplification must be approximately equal. A sensitive method for assessing whether two amplicons have the same amplification efficiency is to see how $\Delta$Ct varies when using a serial dilution of a control cDNA. We performed two validations: one using control cDNA, another using cDNA from paraffin-embedded samples. Several runs with serial dilutions were performed to confirm that the slope <0.1 in the plot $\Delta C_t$ value versus $\text{Log}_{10}$ input amount cDNA, defined as Ct BRCA1 in each dilution minus Ct $\beta$-actin in the same dilution (C). For primers and probe sets, the slope of the plot $C_t$ versus $\text{Log}_{10}$ input amount cDNA needed to be between $-3.25$ and $-3.45$, since a slope of $-3.33$ represents 100% efficiency. The slopes in our assays were $-3.36$ for $\beta$-actin and $-3.32$ for BRCA1, with a correlation coefficient ($R^2$)>0.98 (D).
Figure 1B:
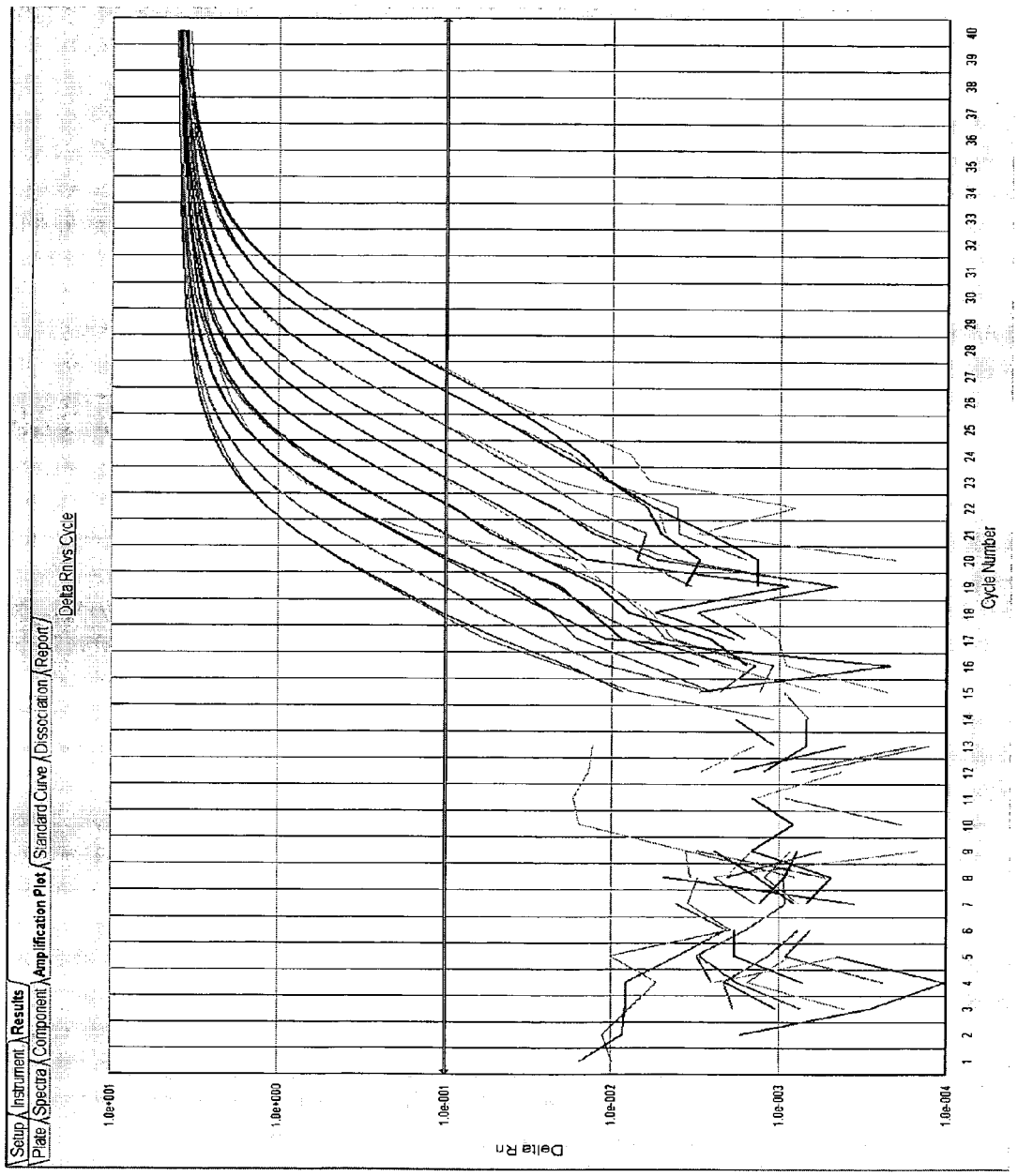
Figure 1C:
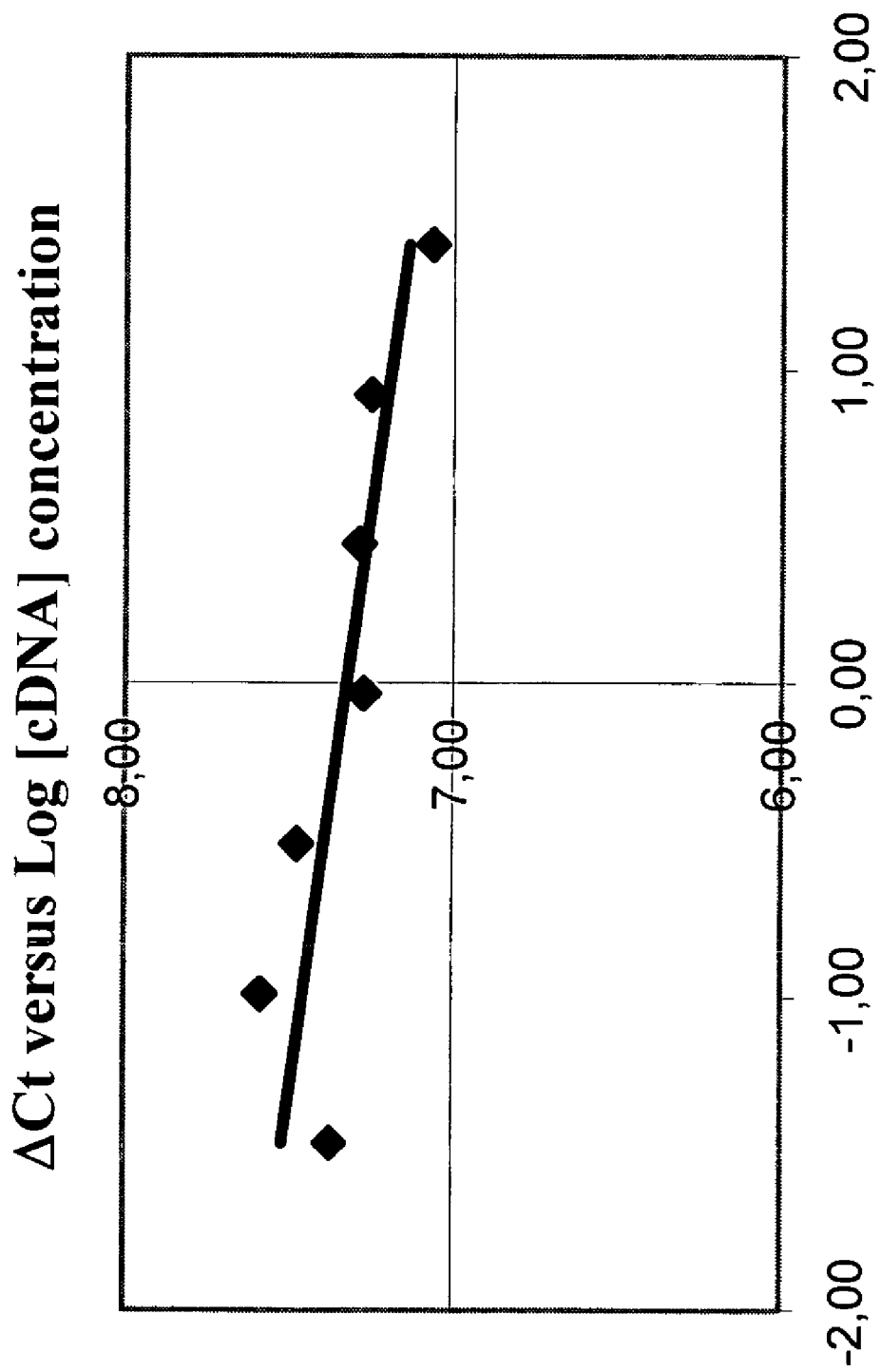
Figure 1D:
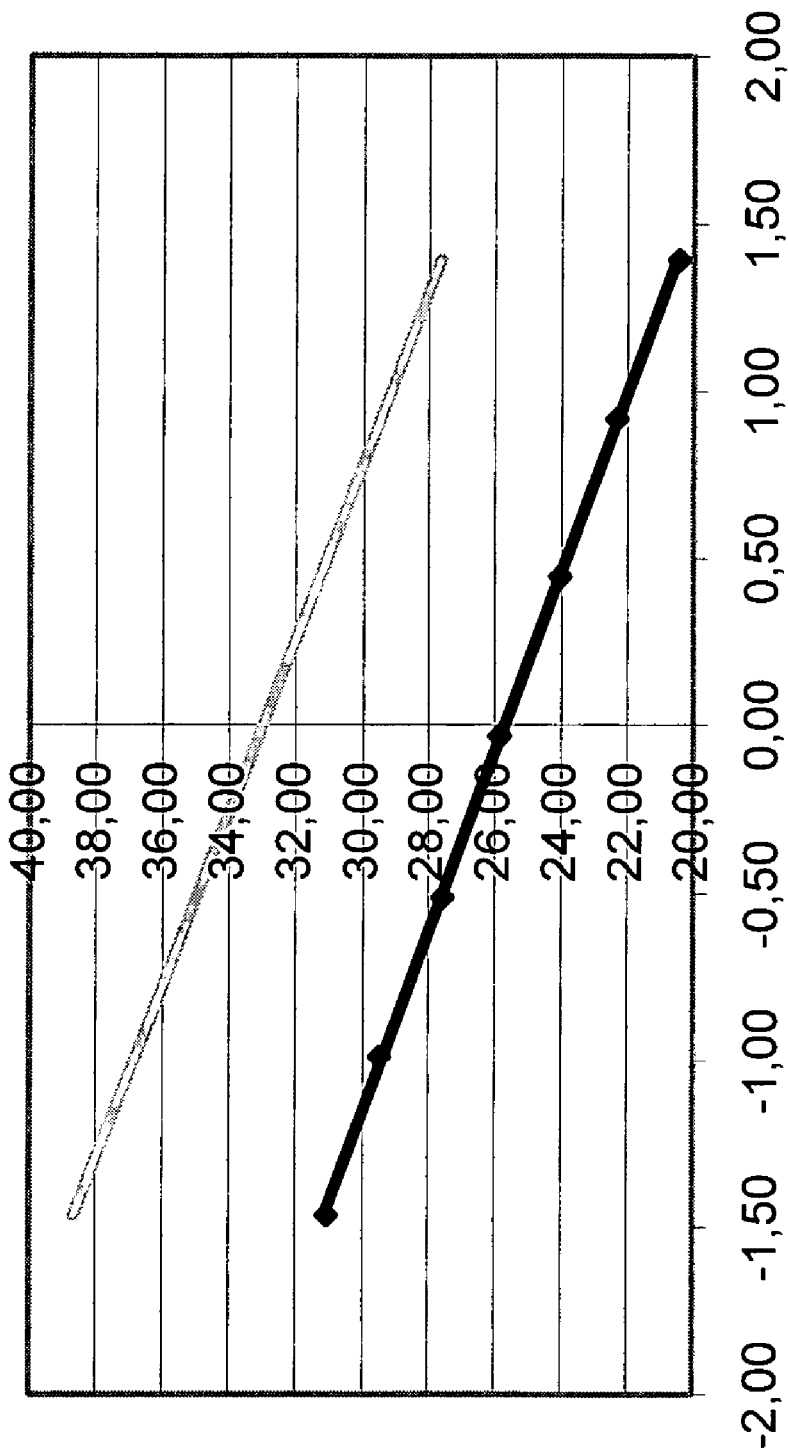

Based on the evidence for the role of BRCA1 in breast and ovarian cancer, we investigated if BRCA1 mRNA expression could also play an important role in predicting differential chemotherapy sensitivity in lung cancer, in particular NSCLC. The resistance of tumor cells to cytotoxic chemotherapeutic agents, especially antimetabolites such as gemcitabine and agents that damage DNA in the manner of platinating agents has been assayed by examining the mRNA expressed from genes involved in nucleotide synthesis and DNA repair in humans.

The present invention resides in part in the finding that the amount of BRCA1 mRNA is correlated with resistance to cisplatin agents. Tumors expressing high levels of BRCA1 mRNA are considered likely to be resistant to platinum-based chemotherapy. On the other hand, those tumors expressing low amounts of BRCA1 mRNA are likely to be sensitive to platinum-based chemotherapy. A patient's tumor BRCA1 mRNA expression level is judged by comparing it to a predetermined threshold expression level.

We examined the potential predictive value of BRCA1 mRNA expression in resected specimens from stage IIB, IIIA and IIIB NSCLC patients treated with neoadjuvant gemcitabine/cisplatin followed by surgery. Surprisingly, we found that there is a correlation and that BRCA1 is a predictive marker of differential chemosensitivity and BRCA1 mRNA assessment provides an important method for customizing NSCLC chemotherapy.

The present method can be applied to any type of tissue from a patient. For examination of resistance of tumor tissue, it is preferable to examine the tumor tissue. In a preferred embodiment, a portion of normal tissue from the patient from which the tumor is obtained, is also examined. Preferably this is done prior to the chemotherapy.

In performing the methods of the present invention, tumor cells are preferably isolated from the patient. Tumors or portions thereof are surgically resected from the patient or obtained by routine biopsy. RNA isolated from frozen or fresh samples is extracted from the cells by any of the methods typical in the art, for example, Sambrook, Fischer and Maniatis, Molecular Cloning, a laboratory manual, (2nd ed.), Cold Spring Harbor Laboratory Press, New York, (1989). Preferably, care is taken to avoid degradation of the RNA during the extraction process.

In a particular embodiment, the expression level is determined using RNA obtained from a formalin-fixed, paraffin-embedded tissue sample. Other tissue samples are envisaged, such as fresh tissue from a biopsy or blood samples depending on their availability.

Fixed and paraffin-embedded tissue samples are preferred because they are broadly available from tissue sample archives in the field of Oncology. RNA may be isolated from an archival pathological sample or biopsy sample which is first deparaffinized. An exemplary deparaffinization method involves washing the paraffinized sample with an organic solvent, such as xylene, for example. Deparaffinized samples can be rehydrated with an aqueous solution of a lower alcohol. Suitable lower alcohols, for example include, methanol, ethanol, propanols, and butanols. Deparaffinized samples may be rehydrated with successive washes with lower alcoholic solutions of decreasing concentration, for example. Alternatively, the sample is simultaneously deparaffinized and rehydrated. The sample is then lysed and RNA is extracted from the sample.

While all techniques of gene expression profiling, as well as proteomics techniques, are suitable for use in performing the foregoing aspects of the invention, the gene expression levels are often determined by reverse transcription polymerase chain reaction (RT-PCR).

The values for "low," "normal," or "high" levels of expression are determined by comparison to reproducible standards which correspond to the median value of expression levels of BRCA1 measured in a collection of tumor tissue in biopsy samples from cancer patients, previous to the neoadjuvant chemotherapeutic treatment. Once this median value is established, the level of this marker expressed in tumor tissues from patients can be compared with this median value, and thus be assigned a level of "low," "normal" or "high."

The measure of relative gene expression is preferably made by using β-actin as an endogenous control, although other methods known in the art can be used, as long as relative levels of BRCA1 can be assigned to the samples. Levels of mRNA or the corresponding protein can be measured to obtain the relative level of BRCA1 expression. Standard methods of measurement well known in the art are used, see for example EP 1 381 681 incorporated by reference herein in its entirety.

In one embodiment relative gene expression quantification is calculated according to the comparative Ct method using β-actin as an endogenous control and commercial RNA controls as calibrators. Final results, are determined according to the formula $2^{-(\Delta Ct\ sample - \Delta Ct\ calibrator)}$, where $\Delta C_T$ values of the calibrator and sample are determined by subtracting the $C_T$ value of the target gene from the value of the β-actin gene.

The collection of samples from which the reference level is derived will preferably be constituted from patient suffering from NSCLC. For example, the one described in the examples which is statistically representative was constituted with 55 samples from NSCLC patients. In other cases it can contain a different number of samples.

In one example, we used real-time quantitative PCR to determine BRCA1 mRNA levels in 55 surgically resected tumors of non-small-cell lung cancer patients who had received neoadjuvant gemcitabine/cisplatin chemotherapy, and divided the gene expression values into quartiles. These quartiles represent the different threshold levels. When results were correlated with outcome, median survival was not reached for the 15 patients in the bottom quartile, while for the 28 in the two middle quartiles, it was 37.8 months (95% CI, 10.6-65), and for the 12 patients in the top quartile, it was 12.7 months (95% CI, 0.28-28.8) (P=0.01). Moreover, patients with BRCA1 levels in the bottom quartile and those with levels in the two middle quartiles both had a significantly decreased risk of death compared to those in the top quartile (hazard ratio=0.187 [P=0.008] and 0.382 [P=0.042], respectively).

The chemotherapy agents to be used in the methods of this invention will be administered in doses commonly employed clinically. Such doses will be calculated in the normal fashion, for example on body surface area.

Gemcitabine is the generic name assigned to 2'-deoxy-2', 2'-difluoro-cytidine. It is commercially available as the monohydrochloride salt, and as the beta-isomer. It is also known chemically as 1-(4-amino-2-oxo-1H-pyrimidin-1-yl)-2-desoxy-2,2-difluororibose. Gemcitabine is disclosed in U.S. Pat. Nos. 4,808,614 and 5,464,826, which are incorporated herein by reference. Gemcitabine will likewise be administered at doses comparable to those routinely utilized clinically. For example, the initial dose of gemcitabine, typically as the hydrochloride salt, will be about 1000-1250 mg/m$^2$ of body surface area. This product is routinely formulated as a sterile solution and is administered by intravenous infusion, generally over about a 30-minute period, with about 2 to 4 weekly doses, with courses repeated about every 28 to 30 days. The dose of 1000-1250 mg/m$^2$ can be given for up to about 7 weeks, according to this treatment regimen, or until undesirable side effects are observed. Other salt forms can be utilized if desired, for example, the hydrobromide, monophosphate, sulfate, malonate, citrate, and succinate are readily prepared.

Cisplatin is the generic name for cis-diaminodichloroplatinum and is described in U.S. Pat. No. 5,562,925, which is incorporated herein by reference. Cisplatin generally is formulated as a sterile solution for injection, and is routinely administered at a dose of about 50 to 100 mg/m$^2$, given intravenously. This cycle can be repeated for about every 4 to 8 weeks.

Thus according to the invention the appropriate chemotherapeutic agents for a patient suffering of NSCLC can be selected according to his levels of BRCA1 expression. Patients with low BRCA1 mRNA levels can benefit from single-agent cisplatin, while those with high levels would benefit from single-agent docetaxel or paclitaxel. In contrast, high BRCA1 levels may diminish the synergism between taxanes and cisplatin or carboplatin. While sensitivity to antimetabolites, such as gemcitabine, may not be affected by BRCA1 levels, gemcitabine/cisplatin synergism may be partially abrogated in tumors with high BRCA1 mRNA levels, but these tumors may benefit from the synergism observed between taxanes and gemcitabine.

The invention being thus described, practice of the invention is illustrated by the experimental examples provided below. The skilled practitioner will realize that the materials and methods used in the illustrative examples can be modified in various ways.

EXAMPLES

Patients

In all patients, neoadjuvant chemotherapy was indicated after evaluation by a thoracic surgeon, a radiologist, a medical oncologist, and a radiation oncologist. Patients received three cycles of neoadjuvant chemotherapy; 51 received cisplatin 100 mg/m$^2$ day 1 plus gemcitabine 1250 mg/m$^2$ days 1 and 8 every 21 days, and four received carboplatin AUC=5 day 1 plus gemcitabine 1000 mg/m$^2$ days 1 and 8 every 21 days. A thoracotomy was performed within four to five weeks after the last chemotherapy cycle; the surgical procedure was based on the extent of tumor at the time of the initial presentation.

BRCA1 Gene Expression Analysis by RT-QPCR

We examined BRCA1 gene expression in formalin-fixed, paraffin-embedded surgical resected specimens from the 55 patients as previously described: Specht K, et al. (2001) *Am. J. Pathol.*, 158, 419-429: "Quantitative gene expression analysis in microdissected archival formalin-fixed and paraffin-embedded tumor tissue"; Krafft A E, et al. (1997) *Mol. Diagn.*, 3, 217-230: "Optimization of the isolation and amplification of RNA from formalin fixed, paraffin-embedded tissue: The Armed Forces Institute of Pathology experience and literature review". After standard tissue sample deparaffinization using xylene and alcohols, samples were lysed in a tris-chloride, EDTA, sodium dodecyl sulphate (SDS) and proteinase K containing buffer. RNA was then extracted with phenol-chloroform-isoamyl alcohol followed by precipitation with isopropanol in the presence of glycogen and sodium acetate. RNA was resuspended in RNA storage solution (Ambion Inc; Austin Tex., USA) and treated with DNAse I to avoid DNA contamination. cDNA was synthesized using M-MLV retrotranscriptase enzyme. Template cDNA was added to Taqman Universal Master Mix (AB; Applied Biosystems, Foster City, Calif., USA) in a 12.5-µl reaction with specific primers and probe for each gene. The primer and probe sets were designed using Primer Express 2.0 Software (AB). Quantification of gene expression was performed using the ABI Prism 7900HT Sequence Detection System (AB). Primers and probe for BRCA1 mRNA expression analysis were designed according to the Ref Seq NM_007294 (www.ncbi.nlm.nih.gov/LocusLink). Forward primer is located in exon 8 (position 4292 bp to 4317 bp), reverse primer in exon 9 (position 4336 bp to 4360 bp), and probe in the exon 8/9 junction (position 4313 bp to 4333 bp). The PCR product size generated with these primers was 69 bp. The primers and 5' labeled fluorescent reporter dye (6FAM) probe were as follows: β-actin: forward 5' TGA GCG CGG CTA CAG CTT 3', reverse 5' TCC TTA ATG TCA CGC ACG ATT T 3', probe 5' ACC ACC ACG GCC GAG CGG 3'; BRCA1: forward 5'GGC TAT CCT CTC AGA GTG ACA TTT TA 3', reverse 5' GCT TTA TCA GGT TAT GTT GCA TGG T 3', probe 5' CCA CTC AGC AGA GGG 3'.

Relative gene expression quantification was calculated according to the comparative Ct method using β-actin as an endogenous control and commercial RNA controls (Stratagene, La Jolla, Calif.) as calibrators. Final results, were determined as follows: $2^{-(\Delta Ct\,sample - \Delta Ct\,calibrator)}$, where $\Delta C_T$ values of the calibrator and sample are determined by subtracting the $C_T$ value of the target gene from the value of the β-actin gene. In all experiments, only triplicates with a standard deviation (SD) of the Ct value <0.20 were accepted. In addition, for each sample analyzed, a retrotranscriptase minus control was run in the same plate to assure lack of genomic DNA contamination (FIG. 1).

Statistical Methods

In order to provide an easily interpretable evaluation of the effect of BRCA1 mRNA expression, gene expression values were divided into quartiles. Interpatient variation coefficients were calculated to assess similarities between quartiles. Hazard ratios were calculated with the univariate Cox model, and comparison between Kaplan-Meier survival curves was performed with the log-rank test. All tests of statistical significance were two-sided, with a statistical power of 80%, and significance was set at 0.05 except in multiple comparisons, where it was set at 0.017 in accordance with the Bonferroni correction.

Results

Median survival was 37.8 months (95% CI, 27-48.5 months) for all patients, 51.9 months (95% CI, 31.6-72.4 months) for patients who underwent lobectomy, and 25.8 months (95% CI, 12.7-38.8 months) for those who underwent pneumonectomy. BRCA1 was detected in all tumors, although there was considerable variation in its level of expression, with values relative to the β-actin internal control ranging approximately 37-fold, from 0.28 to 10.43.

Amplification plots obtained for the genes BRCA1 and β-actin are shown in FIG. 1. Values ranged from 0.28 to 0.61 (interpatient coefficient of variation, 30.7%) for the 15 patients in the bottom quartile, from 0.65 to 1.20 (interpatient coefficient of variation, 17.4%) for the 14 patients in the second quartile, from 1.23 to 2.37 (interpatient coefficient of variation, 17.7%) for the 14 patients in the third quartile, and from 2.45 to 10.43 (interpatient coefficient of variation, 54.7%) for the 12 patients in the top quartile. Due to the similar values and interpatient coefficients of variation observed in the second and third quartiles, these two groups were merged for statistical analyses.

No differences in clinical characteristics were observed according to quartiles of BRCA1 mRNA expression levels (Table 1). However, for patients in the bottom quartile, radiographic response tended to be higher than for those in the middle or top quartiles (66.7%, 57.1%, 58.3%, respectively), complete resection was attained more often (93.3%, 78.6%, 83.3%, respectively), and a lobectomy was performed more often (73.3%, 32.1% [P=0.005], 58.3% [P=0.2], respectively).

TABLE 1

Patient characteristics according to BRCA1 mRNA expression levels (bottom quartile vs two middle quartiles vs top quartile)

|  | Bottom Quartile of BRCA1 Levels (0.28-0.61) N (%) | Middle Quartiles of BRCA1 Levels (0.65-2.37) N (%) | Top Quartile of BRCA1 Levels (2.45-10.43) N (%) |
|---|---|---|---|
| Sex |  |  |  |
| Female | 3 (20) | 3 (10.7) | 0 |
| Male | 12 (80) | 25 (89.3) | 12 (100) |
| Age |  |  |  |

TABLE 1-continued

Patient characteristics according to BRCA1 mRNA expression levels (bottom quartile vs two middle quartiles vs top quartile)

| | Bottom Quartile of BRCA1 Levels (0.28-0.61) N (%) | Middle Quartiles of BRCA1 Levels (0.65-2.37) N (%) | Top Quartile of BRCA1 Levels (2.45-10.43) N (%) |
|---|---|---|---|
| Median, range | 60 (49-74) | 65 (51-76) | 61 (45-71) |
| Histology | | | |
| Squamous cell carcinoma | 5 (33.3) | 16 (57.1) | 5 (41.7) |
| Adenocarcinoma | 7 (46.7) | 11 (39.3) | 2 (16.7) |
| Large cell carcinoma | 3 (20) | 1 (3.6) | 5 (41.7) |
| Initial staging | | | |
| IIB: T3N0 | 2 (13.3) | 3 (10.7) | 1 (8.3) |
| IIIA: | | | |
| T3N1 | 0 | 1 (3.6) | 3 (25) |
| T1N2 | 0 | 0 | 0 |
| T2N2 | 1 (6.7) | 6 (21.4) | 1 (8.3) |
| T3N2 | 3 (20) | 7 (25) | 2 (16.7) |
| IIIB: | | | |
| T4N0 | 6 (40) | 8 (28.6) | 3 (25) |
| T4N1 | 1 (6.7) | 2 (7.1) | 1 (8.3) |
| T4N2 | 2 (13.3) | 1 (3.6) | 1 (8.3) |
| Chemotherapy Regimen | | | |
| Gemcitabine/Cisplatin | 15 (100) | 26 (92.9) | 10 (83.3) |
| Gemcitabine/Carboplatin | 0 | 2 (7.1) | 2 (16.7) |
| Radiographic Response | | | |
| Partial Response | 10 (66.7) | 16 (57.1) | 7 (58.3) |
| Stable Disease | 5 (33.3) | 10 (35.7) | 4 (33.3) |
| Progressive Disease | 0 | 2 (7.1) | 1 (8.3) |
| Surgical Results | | | |
| Complete Resection | 14 (93.3) | 22 (78.6) | 10 (83.3) |
| Incomplete Resection | 1 (6.7) | 5 (17.9) | 2 (16.7) |
| Unresectable | 0 | 1 (3.6) | 0 |
| Surgical Procedures | | | |
| Lobectomy | 11 (73.3) | 9 (32.1) | 7 (58.3) |
| Pneumonectomy | 4 (26.7) | 14 (50) | 5 (41.7) |
| Bilobectomy | 0 | 4 (14.3) | 0 |
| Unresectable | 0 | 1 (3.6) | 0 |

Figure 2:
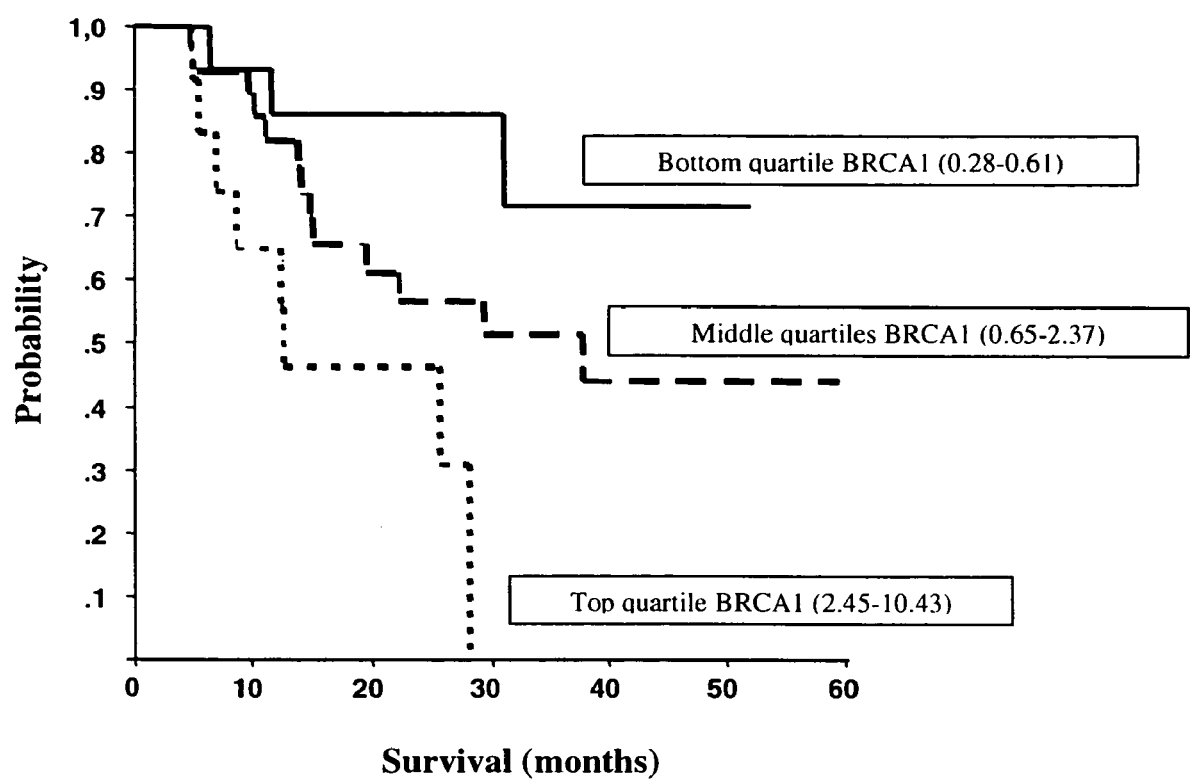
FIG. 2. Median survival according to quartiles of BRCA1 mRNA expression levels. Median survival was not reached for those in the bottom quartile, while it was 37.8 months for those in the middle quartiles, and 12.7 months for those in the top quartile.

Median survival was not reached for the 15 patients in the bottom quartile, while for the 28 in the two middle quartiles, it was 37.8 months (95% CI, 10.6-65), and for the 12 patients in the top quartile, it was 12.7 months (95% CI, 0.28-28.8) (P=0.01) (FIG. 2). Five patients who attained a complete pathologic response (T0N0) were all in the bottom quartile of BRCA1 levels (Table 2):

TABLE 2

BRCA1 mRNA levels and clinical stage in patients who attained complete pathologic response after neoadjuvant chemotherapy followed by surgery.

| Patient | BRCA1 mRNA Levels | Pre-Treatment Clinical Stage | Post-Treatment Clinical Stage | Pathologic Stage |
|---|---|---|---|---|
| 1 | 0.31 | T3N2 | T2N0 | T0N0 |
| 2 | 0.28 | T2N2 | T1N0 | T0N0 |
| 3 | 0.30 | T4N2 | T2N1 | T0N0 |
| 4 | 0.33 | T4N2 | T2N0 | T0N0 |
| 5 | 0.34 | T4N1 | T4N1 | T0N0 |

Conversely, in the majority of patients with high BRCA1 levels, no clinical or pathologic downstaging was observed following chemotherapy and surgery (Table 3):

TABLE 3

Correlation of clinical and pathologic stage in patients in the top quartile of BRCA1 mRNA expression.

| Patient | mRNA BRCA1 Levels | Pre-Treatment Clinical Stage | Post-Treatment Clinical Stage | Pathologic Stage |
|---|---|---|---|---|
| 1 | 2.8 | T3N2 | T3N2 | T2N2 |
| 2 | 5.5 | T2N2 | —* | T2N0 |
| 3 | 10.43 | T3N1 | T2N0 | T2N0 |
| 4 | 2.45 | T3N0 | T3N0 | T3N0 |
| 5 | 4.12 | T4N0 | T1N0 | T4N0 |
| 6 | 6.93 | T4N2 | T3N0 | T2N0 |
| 7 | 2.81 | T4N1 | T4N1 | T3N1 |
| 8 | 3.09 | T3N1 | T2N0 | T2N0 |
| 9 | 5.61 | T3N1 | T2N0 | T2N0 |
| 10 | 3.36 | T3N2 | T3N2 | T2N2 |
| 11 | 2.8 | T4N0 | T3N0 | T3N0 |
| 12 | 2.62 | T4N0 | T4N0 | T2N0 |

*data not available

When patients were stratified by pathologic stage, those in the bottom quartile had a decreased risk of death (HR=0.206; 95% CI, 0.05-0.83; P=0.026) compared to those in the top quartile, and those in the two middle quartiles also had a decreased risk of death (HR=0.294; 95% CI, 0.10-0.83; P=0.020) compared to those in the top quartile. When patients were stratified by clinical stage, a similar pattern was observed. Those in the bottom quartile had a decreased risk of death (HR=0.220; 95% CI, 0.06-0.77; P=0.018) compared to those in the top quartile, and those in the two middle quartiles also had a decreased risk of death (HR=0.430; 95% CI, 0.17-1.1; P=0.078) compared to those in the top quartile. Thus, patients with low BRCA1 mRNA levels (bottom quartile) obtain the maximum benefit of neoadjuvant gemcitabine/cisplatin chemotherapy.

The invention claimed is:

1. A screening method for selecting an effective chemotherapy for the treatment of a patient suffering from non-small-cell lung cancer (NSCLC), comprising the steps:
    a) isolating mRNA from a cancerous tumor tissue sample of the patient;
    b) determining the mRNA level of BRCA1 in the patient's sample;
    c) classifying the patient as either "low," "normal," or "high" by comparing the BRCA1 mRNA levels in the patient's sample with ranges of BRCA1 mRNA levels previously determined by measuring the BRCA1 mRNA levels of each within a collection of NSCLC tumor tissue biopsy samples previous to neoadjuvant chemotherapeutic treatment, and dividing the BRCA1 mRNA levels of all of the NSCLC tumor tissue biopsy samples into quartiles, wherein the patient is classified as "low" if the BRCA1 mRNA level in the patient's sample is within the range of BRCA1 mRNA levels of the bottom quartile, "high" if the BRCA1 mRNA level is within the range of BRCA1 mRNA levels of the top quartile, and "normal" is the BRCA1 mRNA level is within the range of BRCA1 mRNA levels of the middle two quartiles;
    d) selecting paclitaxel, docetaxel, paclitaxel/gemcitabine or docetaxel/gemcitabine for chemotherapeutic treatment of the patient if the patient is classified a "high" and selecting cisplatin or gemcitabine/cisplatin for chemotherapeutic treatment of the patient if the patient is classified as "low".

2. The method as defined in claim 1 wherein the patient is suffering NSCLC prior to surgery.

3. The method as defined in claim 1 wherein the collection of NSCLC tumor tissue biopsy samples has at least 50 samples.

4. The method as defined in claim 1 wherein the collection of NSCLC tumor tissue biopsy samples has at least 40 samples.

5. The method as defined in any of claim 1, 2, 3, or 4, wherein the patient's sample and each sample within the set of NSCLC tumor tissue biopsy samples are fixed and paraffin-embedded samples.

* * * * *